US010063847B2

(12) United States Patent
Coni et al.

(10) Patent No.: US 10,063,847 B2
(45) Date of Patent: Aug. 28, 2018

(54) MONOCHROMATIC STEREOSCOPIC VIEWING SYSTEM EMPLOYING PROJECTION ONTO A SEMITRANSPARENT PLATE

(71) Applicant: THALES, Courbevoie (FR)

(72) Inventors: Philippe Coni, Saint Jean d'Illac (FR); Laurent Laluque, Bordeaux (FR); Aude Gueguen, Bordeaux (FR)

(73) Assignee: Thales, Courbevoie (FR)

( * ) Notice: Subject to any disclaimer, the term of this patent is extended or adjusted under 35 U.S.C. 154(b) by 304 days.

(21) Appl. No.: 14/862,104

(22) Filed: Sep. 22, 2015

(65) Prior Publication Data
US 2016/0088291 A1    Mar. 24, 2016

(30) Foreign Application Priority Data

Sep. 22, 2014 (FR) .................................... 14 02109

(51) Int. Cl.
*H04N 13/04* (2006.01)
*A61F 9/02* (2006.01)
(Continued)

(52) U.S. Cl.
CPC ......... *H04N 13/0459* (2013.01); *A61F 9/022* (2013.01); *G02B 27/0101* (2013.01);
(Continued)

(58) Field of Classification Search
None
See application file for complete search history.

(56) References Cited

U.S. PATENT DOCUMENTS 4,172,632 A * 10/1979 Holmes, Jr. ........ G02B 27/2207
340/972
4,190,832 A *  2/1980 Mohler ................. B60K 37/00
340/462
(Continued)

FOREIGN PATENT DOCUMENTS

GB           597409 A  *  1/1948  ............. G03B 41/08
WO    WO 2005/039192 A1    4/2005

OTHER PUBLICATIONS

French Search Report for corresponding French Patent Application No. 1402109, 8 pp., (dated Jun. 19, 2015).
(Continued)

*Primary Examiner* — Janese Duley
(74) *Attorney, Agent, or Firm* — Womble Bond Dickinson (US) LLP

(57) ABSTRACT

The field of the invention is that of viewing systems comprising means for generating stereoscopic images, a viewing device comprising a projector and a semitransparent screen and a pair of stereoscopic glasses. The projector according to the invention comprises means arranged so as to project alternatively a first image emitted at a first wavelength and a second image emitted at a second wavelength different from the first wavelength. The pair of glasses comprises a first filter and a second filter, the first filter transmitting the entirety of the spectrum except a first narrow spectral band centered on the first wavelength and the second filter transmitting the entirety of the spectrum except a second narrow spectral band centered on the second wavelength.

8 Claims, 4 Drawing Sheets

(51) Int. Cl.
*G02B 27/22* (2018.01)
*G02B 27/01* (2006.01)
(52) U.S. Cl.
CPC ..... *G02B 27/2207* (2013.01); *G02B 27/2264* (2013.01); *H04N 13/0429* (2013.01); *H04N 13/0431* (2013.01); *H04N 13/0434* (2013.01); *H04N 13/0438* (2013.01); *G02B 2027/0114* (2013.01); *G02B 2027/0134* (2013.01); *G02B 2027/0167* (2013.01)

(56) References Cited

U.S. PATENT DOCUMENTS

| | | | | |
|---|---|---|---|---|
| 6,283,597 | B1 | 9/2001 | Jorke | |
| 2006/0098093 | A1* | 5/2006 | Hahn | H04N 13/0239 348/148 |
| 2007/0009222 | A1* | 1/2007 | Koo | G02B 27/2278 385/147 |
| 2007/0127121 | A1* | 6/2007 | Maximus | G02B 26/007 359/465 |
| 2010/0208041 | A1* | 8/2010 | Savvateev | G02B 27/2207 348/51 |
| 2011/0019152 | A1* | 1/2011 | Shestak | G03B 21/006 353/7 |
| 2011/0205494 | A1 | 8/2011 | Richards et al. | |
| 2013/0182322 | A1* | 7/2013 | Silverstein | G02C 7/107 359/464 |
| 2013/0342904 | A1 | 12/2013 | Richards | |
| 2014/0009827 | A1* | 1/2014 | Simon | G02B 5/28 359/464 |
| 2014/0022637 | A1 | 1/2014 | Richards et al. | |

OTHER PUBLICATIONS

European Patent Office Communication enclosing the European Search Report for corresponding European Patent Application No. 15186146.5, 6 pp., (dated Feb. 3, 2016).

Patrick Murphy, "Lasers and Aviation Safety", International Laser Display Association, Version 2.2, 18 pp., (Sep. 10, 2009).

* cited by examiner

MONOCHROMATIC STEREOSCOPIC VIEWING SYSTEM EMPLOYING PROJECTION ONTO A SEMITRANSPARENT PLATE

CROSS-REFERENCE TO RELATED APPLICATIONS

This application claims foreign priority to French Patent App. No. 1402109, filed 22 Sep. 2014.

FIELD OF THE INVENTION

The field of the invention is that of viewing systems allowing an image to be superposed on the outside world. The technical applications are mainly in vehicular piloting/driving assistance systems. The invention more particularly applies to the field of aircraft cockpits in which the pilot needs to see the exterior and simultaneously view aircraft flight and navigation data. The invention may also be applied to any piloting/driving or control system displaying symbols in superposition on a natural exterior environment. This is the case, for example, for control towers or ship helm stations. The exterior environment may also be simulated. This is the case for driving simulators or drone command/control platforms.

BACKGROUND

There are various types of viewing systems allowing a synthetic image to be superposed on an exterior environment. One possible solution, illustrated in FIG. 1, consists in employing a projector of stereoscopic images. The viewing system 10 then comprises:
- a projector 11 of what are called "3D" stereoscopic images, said projector being capable of generating at least two images referred to as "right eye"/"left eye" images, representative of a given object. In the case in FIG. 1, the object is a sphere S;
- a scattering semitransparent screen 12 onto which the "right eye"/"left eye" images are projected;
- a pair of glasses 13 comprising means for separating the "right eye"/"left eye" images and first detecting means 14 and intended to be worn by a user;
- second detecting means 15 associated with a fixed coordinate system R and that, in combination with the first detecting means 14, allow the spatial position of the pair of glasses 13 to be detected in this fixed coordinate system; and
- an electronic processor 16 performing at least the following functions:
    - acquisition of signals issued from the detecting means 14 and/or 15 and calculation of the position of the pair of glasses;
    - calculation of the position of the stereoscopic image corresponding to the position of the pair of glasses; and
    - calculation of the two right eye/left eye images.

There are various means for achieving the stereoscopic separation of the projected images.

In a first technical solution, temporal separation is used. The projector transmits sequentially and synchronously first the right eye image then the left eye image. The glasses are active and comprise active shutters that are synchronized with the projector. Thus, each eye perceives the image that is intended therefor and only said image. The shutters are generally produced in a technology based on liquid crystals. However, this solution has a number of drawbacks.

The active glasses require a power supply and control electronics and this raises maintenance issues in the context of use on board a vehicle. In addition, the polarizers of the LCD shutters obscure and may even completely obstruct the user's view of the cockpit, depending on the various polarization directions and the inclination of the glasses. Lastly, the presence of polarizers and the left-right vision alternation required to achieve the stereoscopic vision effect leads to loss of a substantial amount of light. The transmission of the glasses is thus no higher than 30%, resulting in a completely unacceptable darkening of the exterior landscape.

In a second technical solution, the stereoscopic projector functions in a polarized mode. It emits in succession and periodically a right eye image with a first polarization and a left eye image with a second polarization that is different from the first polarization. The pair of glasses 13 is passive. It comprises a first polarized eyeglass transparent at the first polarization and opaque at the second and a second polarized eyeglass transparent to the second polarization and opaque at the first.

The polarizer glasses are passive and solve the underlying problem of alternate occultation of each eye, and the management of batteries. In contrast, it is essential to use a silvered polarization-preserving projection screen. Since this screen is not transparent, it is not suitable for the applications concerned by the invention.

In a third technical solution, the projector emits two coloured images the emission spectra of which are separate. The pair of glasses comprises two different filters, the first transmits the first spectrum and filters the second spectrum. The second filter carries out the inverse function. Thus, each eye perceives one and only one coloured image and only said image. This technique is known by the name "anaglyph". The simplest way of producing an anaglyph is to separate the visible spectrum into two portions, one red and the other blue. The obvious advantage of this device is how simple it is to implement, but vision of the exterior world is substantially altered.

Better still, the system referred to as spectral multiplexing separates the visible spectrum into two interlaced portions, one dedicated to each eye. However, although the perceived colour of the landscape is better preserved, its luminance is considerably decreased. The patent applications of Dolby Laboratories Licensing Corporation US 2011/0205494, US 2013/0342904 and US 2014/0022637 describe solutions of this type for cinematographic applications that require neither high light levels nor, of course, an exterior landscape to be transmitted.

SUMMARY

The system according to the invention does not have these drawbacks. It is based on the fact that, for a certain number of applications, the use of coloured images is not necessary. In the field of the superposition of images on an exterior landscape, it may be preferable to use a monochromatic symbology that will perfectly detach from the exterior background rather than a coloured image that risks causing confusion as regards perception of the landscape. The system according to the invention employs monochromatic stereoscopic images emitted at wavelengths that are different but sufficiently close together to give the same coloured visual sensation.

More precisely, the subject of the invention is a viewing system comprising means for generating stereoscopic images of a preset object, a device for viewing said stereoscopic images comprising a projector of stereoscopic images and a semitransparent screen and a pair of stereoscopic glasses, the means for generating stereoscopic images, the viewing device, the semitransparent screen and the pair of stereoscopic glasses being arranged so that the stereoscopic image of the preset object appears, through the stereoscopic glasses, at a preset distance from the semitransparent screen; characterized in that:

the projector comprises means arranged so as to project alternatively a first image emitted at one and only one first wavelength and a second image emitted at one and only one second wavelength different from the first wavelength; and the pair of glasses comprises a first filter placed in front of the right eye and a second filter placed in front of the left eye, the first filter transmitting the entirety of the spectrum except a first narrow spectral band centred on the first wavelength and the second filter transmitting the entirety of the spectrum except a second narrow spectral band centred on the second wavelength.

Advantageously, the first wavelength is separated from the second wavelength by a spectral distance of about 10 to 30 nanometers.

Advantageously, the first wavelength and the second wavelength are located between 500 nanometers and 560 nanometers.

Advantageously, the full-width at half maximum of the first spectral band and of the second spectral band is comprised between 10 nanometers and 30 nanometers.

Advantageously, the projector comprises at least one matrix display illuminated alternatively by two sources emitting at the first wavelength and at the second wavelength, respectively.

Advantageously, the pair of glasses comprises a third filter at one of the wavelengths emitted by the mass-market laser pointers of classes 3A, 3B and 4.

Advantageously, the first spectral band and the second spectral band partially overlap, one of the wavelengths emitted by the mass-market laser pointers of classes 3A, 3B and 4 being located in said zone of overlap so as to be filtered by the first filter and by the second filter.

Advantageously, the system comprises means for detecting the relative position of the pair of glasses with respect to the position of the semitransparent screen and means for calculating stereoscopic images so that the position of the stereoscopic image of the object is stationary in a preset coordinate system and independent of the position of the stereoscopic glasses.

Advantageously, the preset distance is comprised between a few centimeters and optical infinity.

Advantageously, the projector comprises means for displaying a third non-stereoscopic image.

Advantageously, the viewing system is an aircraft cockpit system.

BRIEF DESCRIPTION OF THE DRAWINGS

The invention will be better understood and other advantages will become apparent on reading the following non-limiting description, which is given with reference to the appended figures, in which.

DETAILED DESCRIPTION

Figure 1:
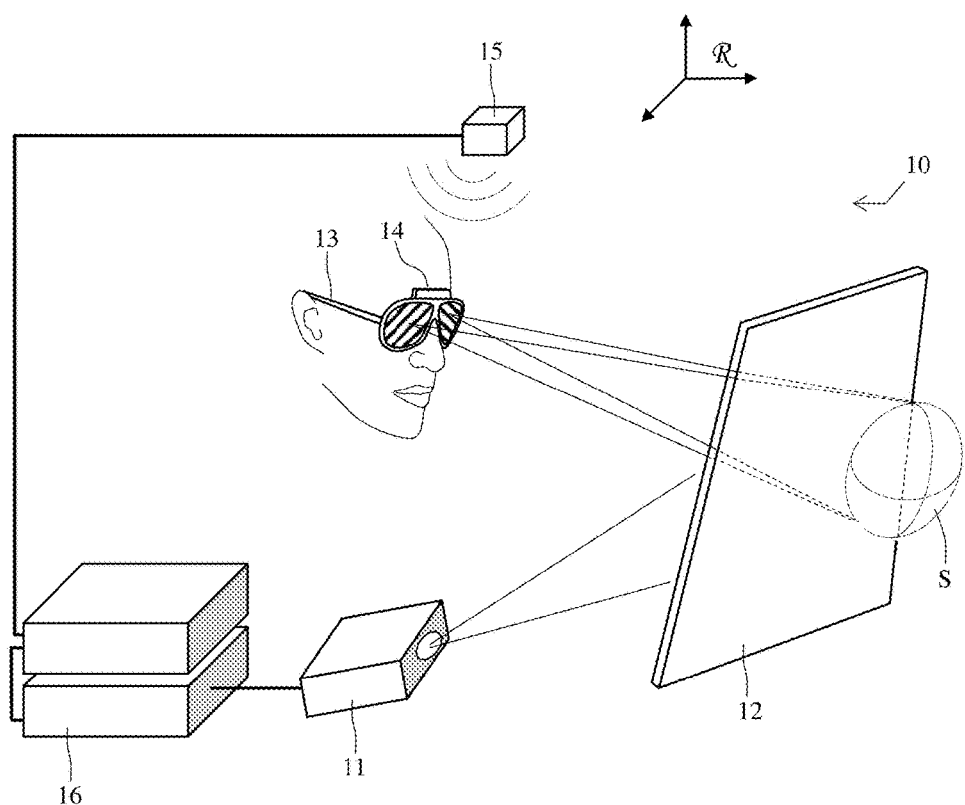
FIG. 1 shows an architecture of a viewing system according to the prior art.
Figure 2:
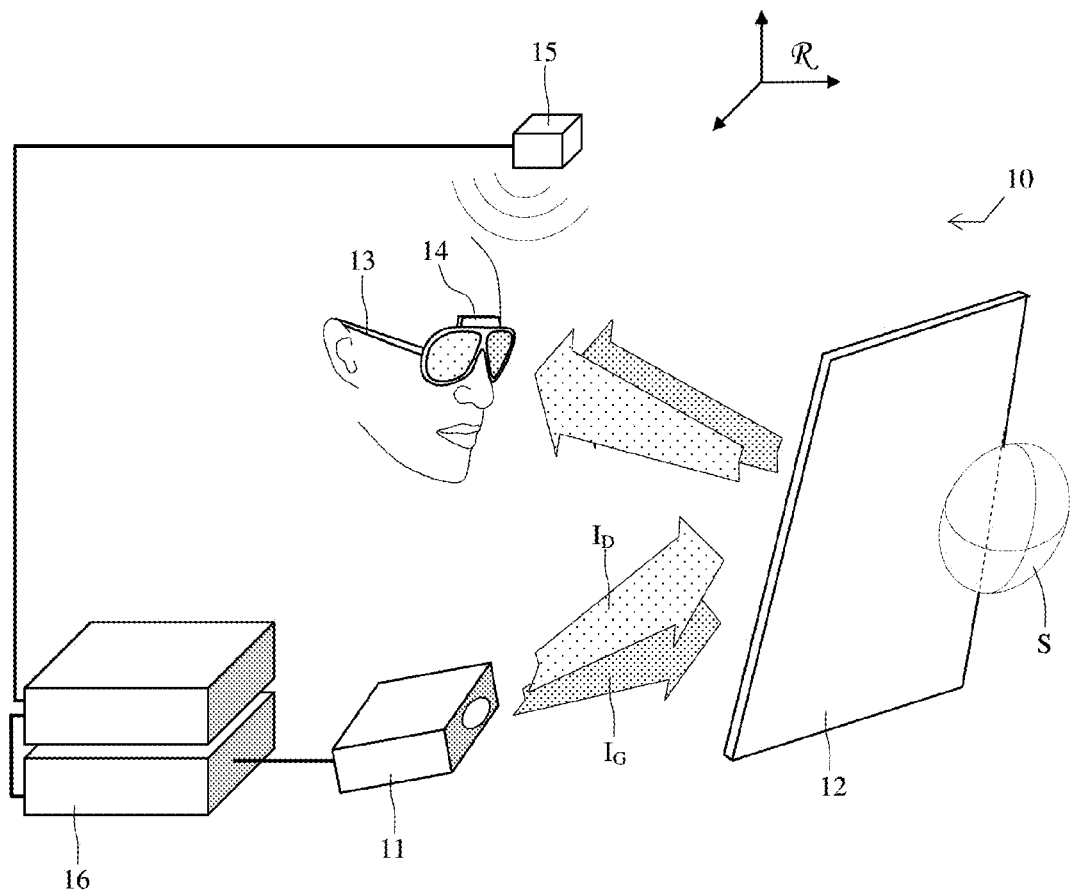
FIG. 2 shows an architecture of a viewing system according to the invention.

By way of example, a viewing system according to the invention is shown in FIG. 2. It comprises at least:

a projector 11 of monochromatic stereoscopic images comprising a high-resolution display and projection optics having a sufficient magnification to cover the semitransparent screen. For aeronautical applications, it is important for the maximum luminance of the display to be able to be very high;

a semitransparent screen 12. This screen 12 is an optical plate that not only is semitransparent to the exterior landscape but also scatters the stereoscopic images. To this end, the surface of the projection screen may comprise an array of scattering patterns. The screen scatters over a wide viewing angle, approximately the half-space. Thus a large eye box is obtained. The expression "eye box" is understood to mean the region of space in which the image is visible. This solution also makes it possible to perfectly control the transparency of the screen. Thus, if the patterns cover only a limited percentage of the surface of the screen, the transmission of the screen is equal to unity minus the percentage covered by the patterns. For example, if the patterns cover 20% of the surface, the transmission of the screen is approximately 80%. It will be noted that, in so far as the projector emits monochromatic images, it is possible to adapt the coefficient of reflection of the patterns so that they are perfectly reflective in the range of emission wavelengths and perfectly transparent outside of this range; and a pair of spectral filter-comprising stereoscopic glasses worn by the user.

The viewing system operates as follows. The display alternately displays two stereoscopic images $I_G$ and $I_D$ representing an object that is a sphere S in FIG. 2, the first is illuminated at a first wavelength and the second image is illuminated at a second wavelength. These two wavelengths neighbour each other but are different. By way of example, the first wavelength is separated from the second wavelength by a spectral distance of about a few nanometers to 30 nanometers. The first wavelength and the second wavelength are located between 500 nanometers and 560 nanometers. For example, the first source may emit at 520 nanometers and the second source at 540 nanometers.

Modulatable emission sources emitting at such wavelengths, using, for example, filtered light-emitting diodes or laser diodes, are readily available. It is also possible to use white light sources filtered into a plurality of spectral bands.

The pair of glasses comprises a first filter placed in front of the right eye and a second filter placed in front of the left eye, the first filter transmitting the entirety of the spectrum except a first narrow spectral band centred on the first wavelength and the second filter transmitting the entirety of the spectrum except a second narrow spectral band centred on the second wavelength, the first spectral band and the second spectral band not overlapping.

Figure 3:
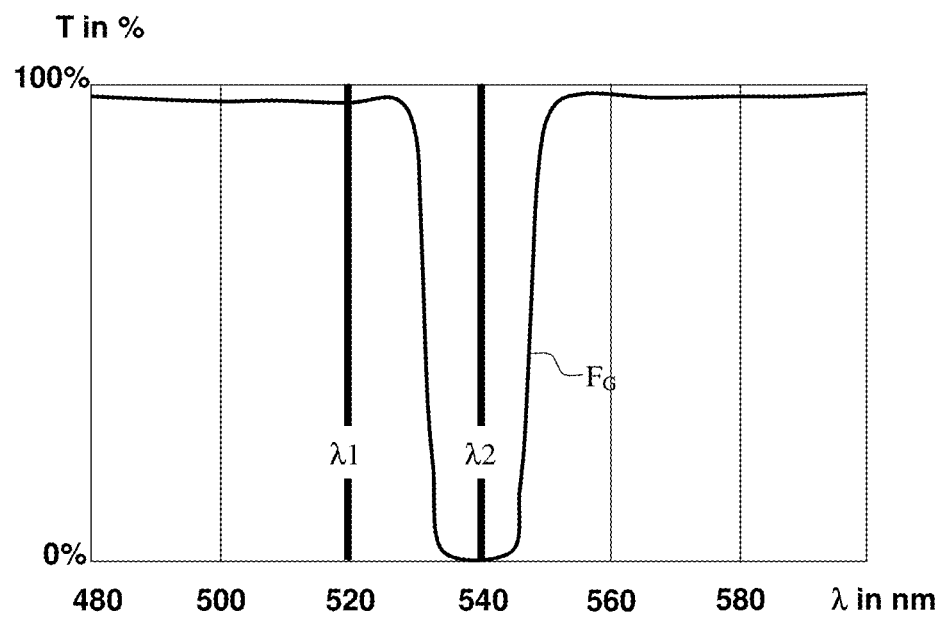
FIG. 3 shows the transmittance of the first filter of the stereoscopic glasses as a function of wavelength and the location of the two emission wavelengths.
Figure 4:
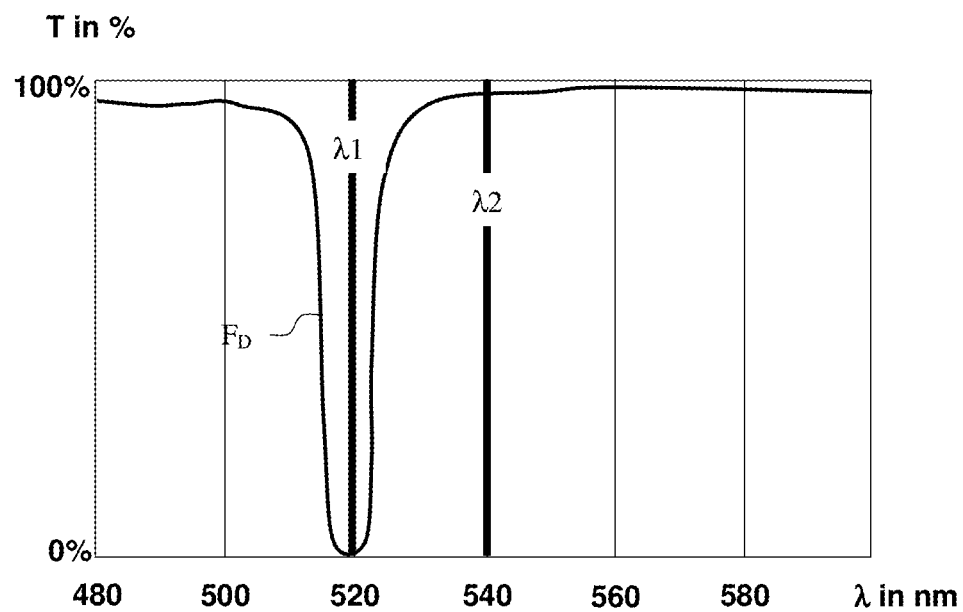
FIG. 4 shows the transmittance of the second filter of the stereoscopic glasses as a function of wavelength and the location of the two emission wavelengths.

By way of example, FIGS. 3 and 4 show the transmittance of the first filter $F_G$ and of the second filter $F_D$ as a function of wavelength and the location of the two emission wavelengths λ1 and λ2 that are located at 520 and 540 nanometers, respectively. The first filter $F_G$ transmits the first wavelength and completely cuts off the second. The second filter $F_D$ transmits the second wavelength and completely cuts off the first. Production of such optical filters presents no particular difficulty. They are known as "notch" filters.

Thus, the left eye can see only the image emitted at the first wavelength and the right eye can see only the image emitted at the second wavelength. The successive stereoscopic images are effectively separated and the stereoscopic illusion is recreated. The user perceives a fused image virtually placed at a certain distance from the viewing screen, this distance possibly being infinity for certain applications. The object may be two-dimensional if it is, for example, a question of a symbol, or three-dimensional.

The system then allows objects to be generated in a very wide range of distances ranging from infinity to distances very close to the user. Thus, the stereoscopic image may represent an object placed in front of the semitransparent screen.

One substantial advantage of this system is that the pair of stereoscopic glasses has an excellent transmission in contrast to the systems of the prior art. Specifically, only a narrow spectral band of the exterior landscape is blocked by the filters.

Figure 5:
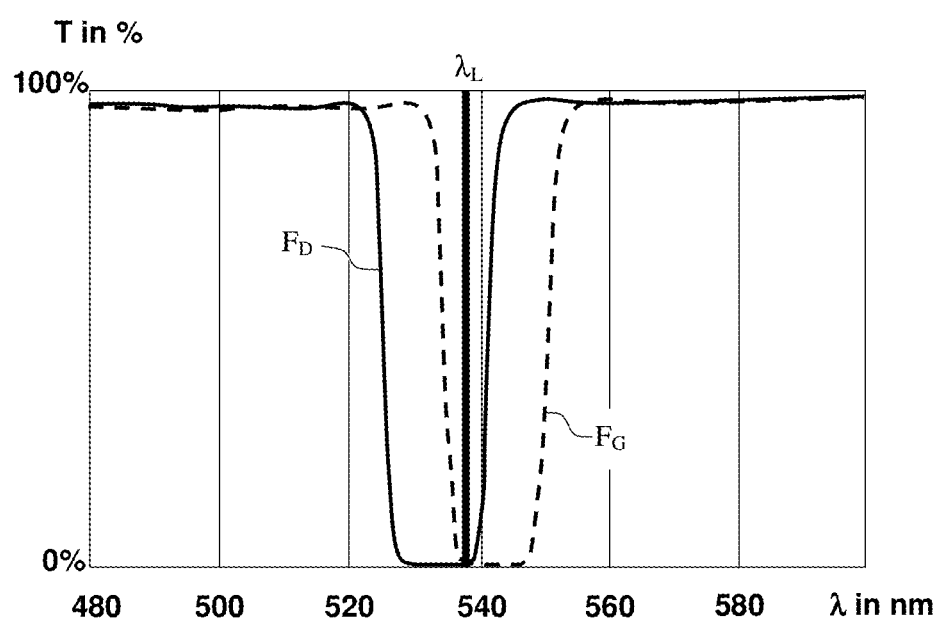
FIG. 5 shows a particular arrangement of the first filter and the second filter allowing conjointly a wavelength and a particular spectral band to be eliminated.

Another advantage is that it is possible to filter one of the wavelengths emitted by mass-market laser pointers of classes 3A, 3B and 4 so as to protect the user from these pointers. One possible solution is to add to the filters of the stereoscopic system an additional filter that blocks this wavelength. Another possible solution is illustrated in FIG. 5. The first spectral band of the first filter $F_G$ and the second spectral band of the second filter $F_D$ partially overlap, said wavelength $λ_L$ emitted by a mass-market laser pointer being located in said zone of overlap so as to be filtered by the first filter and by the second filter. With the latter solution, it is not necessary to add specific filters.

The system according to the invention may comprise a system for detecting the position of the pair of glasses. This type of detecting system conventionally comprises two subassemblies, as may be seen in FIG. 2; a first subassembly 14 fastened to the pair of glasses, and a second subassembly 15 placed in a fixed coordinate system. There are various techniques allowing an object to be located in space. It is possible to use electromagnetic detection. An emitter is placed in the fixed coordinate system and a receiver in the mobile coordinate system. It is also possible to use optical detection which may be passive or active. In the latter case, the pair of glasses has light-emitting diodes the position of the emission of which is located by cameras. All these techniques are known to those skilled in the art. They are compatible with operation in real-time and are easily adaptable to the viewing system according to the invention.

When the user moves his head, his movements are sensed by the detecting means of the pair of glasses. The electronic processor then recalculates in real-time the position of the stereoscopic images so that the user continues to see the virtual image of the object in the same place. To give a simple example, if the virtual image of the object is at infinity, the stereoscopic right eye and left eye images are separated by a distance that is substantially equal to the average interpupillary distance of a human being. Their movement over the viewing screen is substantially equal to that of the pair of glasses. Thus, the sensation of an image at infinity is created.

The viewing system according to the invention also allows non-stereoscopic images to be easily generated. It is enough for these images to be emitted in a red spectral band, a blue spectral band and a third green spectral band of sufficient width to be transmitted by the two filters of the stereoscopic pair of glasses without disrupting vision of the colours.

The technical applications of the viewing system according to the invention are mainly in vehicular piloting/driving assistance systems. The system according to the invention is most particularly applicable to the field of aircraft cockpits in which the pilot needs both to see the exterior and to view aircraft flight and navigation data. The application to the field of helicopters is of particular interest in so far as helicopters possess large windows and are required to carry out flights at low altitudes.

What is claimed is:

1. A viewing system comprising means for generating stereoscopic images of a preset object, a device for viewing said stereoscopic images comprising a projector of stereoscopic images and a semitransparent screen and a pair of stereoscopic glasses, the means for generating stereoscopic images, the viewing device, the semitransparent screen and the pair of stereoscopic glasses being arranged so that the stereoscopic image of the preset object appears, through the stereoscopic glasses, at a preset distance from the semitransparent screen;

wherein:

the projector to project alternatively a first image emitted at one and only one first wavelength and a second image emitted at one and only one second wavelength different from the first wavelength; and the pair of glasses comprises:

a first filter placed in front of a right eye and a second filter placed in front of a left eye, the first filter transmitting an entirety of a spectrum except a first narrow spectral band centred on the first wavelength and the second filter transmitting the entirety of the spectrum except a second narrow spectral band centred on the second wavelength, and the first narrow spectral band and the second narrow spectral band partially overlap between wavelengths of 530 nanometers and 540 nanometers, the wavelengths emitted in said zone of overlap by mass-market laser pointers of at least class 3A being filtered by the first filter and by the second filter.

2. The viewing system according to claim 1, wherein the first wavelength is separated from the second wavelength by a spectral distance between 10 and 30 nanometers.

3. The viewing system according to claim 1, wherein the first wavelength and the second wavelength are located between 500 nanometers and 560 nanometers.

4. The viewing system according to claim 1, wherein the projector comprises at least one matrix display illuminated alternatively by two sources emitting at the first wavelength and at the second wavelength, respectively.

5. The viewing system according to claim 1, wherein the system comprises means for detecting a relative position of the pair of stereoscopic glasses with respect to a position of the semitransparent screen and means for calculating stereoscopic images so that a position of the stereoscopic image of the object is stationary in a preset coordinate system and independent of the relative position of the stereoscopic glasses.

6. The viewing system according to claim 1, wherein the preset distance is comprised between a few centimeters and optical infinity.

7. The viewing system according to claim 1, wherein the projector comprises means for displaying a third non-stereoscopic image.

8. The viewing system according to claim 1, wherein the viewing system is an aircraft cockpit system.

* * * * *